United States Patent [19]
Zigler et al.

[11] Patent Number: 6,001,853
[45] Date of Patent: Dec. 14, 1999

[54] HYDROXYLAMINE COMPOSITIONS FOR THE PREVENTION OR RETARDATION OF CATARACTS

[75] Inventors: J. Samuel Zigler, Middletown; Paul Russell, Bethesda; Santa Tumminia, Ellicott City, all of Md.; Chuan Qin, Somerville, Mass.; C. Murali Krishna, Derwood, Md.

[73] Assignee: The United States of America as represented by the Department of Health and Human Services, Washington, D.C.

[21] Appl. No.: 09/117,068
[22] PCT Filed: Jan. 24, 1997
[86] PCT No.: PCT/US97/01105
  § 371 Date: Jul. 21, 1998
  § 102(e) Date: Jul. 21, 1998
[87] PCT Pub. No.: WO97/26879
  PCT Pub. Date: Jul. 31, 1997

Related U.S. Application Data
[60] Provisional application No. 60/010,637, Jan. 26, 1997.
[51] Int. Cl.$^6$ .......................... A61K 31/445; A61K 31/42
[52] U.S. Cl. ............................ 514/315; 514/374; 514/912
[58] Field of Search ................................. 514/315, 374, 514/912

[56] References Cited

U.S. PATENT DOCUMENTS

| | | |
|---|---|---|
| 5,061,734 | 10/1991 | Mao et al. . |
| 5,118,679 | 6/1992 | Sato et al. . |
| 5,321,138 | 6/1994 | Spector et al. . |
| 5,462,946 | 10/1995 | Mitchell et al. . |
| 5,519,054 | 5/1996 | Santangelo et al. . |

FOREIGN PATENT DOCUMENTS

| | | |
|---|---|---|
| 723305 | 9/1995 | Japan . |
| WO 88/05044 | 7/1988 | WIPO . |
| WO 91/13619 | 9/1991 | WIPO . |
| WO 96/29974 | 10/1996 | WIPO . |
| WO 97/26879 | 7/1997 | WIPO . |

OTHER PUBLICATIONS

Lorand et al., Inhibition of β–Crystallin Cross–Linking in the $Ca^{2+}$–Treated Lens, *Investigative Ophthalmology and Visual Science* 28:1218–1222 (1987).

Lucas, V.A. and Zigler, J.S., Transmembrane Glucose Carriers in the Monkey Lens, *Investigative Ophthalmology and Visual Science* 28:1404–1412 (1987).

Mitchell et al., Inhibition of Oxygen–Dependent Radiation–Induced Damage by the Nitroxide Superoxide Dismutase Mimic, Tempol, *Archives of Biochemistry and Biophysics* 289:62–70 (1991).

Nilsson et al., Inhibition of Lipid Peroxidation by Spin Labels, *Journal of Biological Chemistry* 19:11131–11135 (1989).

Nishigari et al., Effect of MPG on Glucocorticoid–Induced Cataract Formation in Developing Chick Embryo, *Investigative Ophthalmology and Visual Science*, 25:1051–1055 (1984).

Rao et al., Identification and Characterization of the Enzymatic Activity of ζ–Crystallin from Guinea Pig Lens, *The Journal of Biological Chemistry* 267:96–102 (1992).

Reddan et al., The Superoxide Dismutase Mimic TEMPOL Protects Cultured Rabbit Lens Epithelial Cells from Hydrogen Peroxide Insult, *Exp. Eye Res.* 56:543–554 (1993).

Rice–Evans, C.A. and Diplock, A.T., Current Status of Antioxidant Therapy, *Free Radical Biology and Medicine* 15:77–96 (1993).

Tumminia et al., The Integrity of Mammalian Lenses in Organ Culture, *Exp. Eye Res.* 58:367–374 (1994).

Xu et al., Establishment of a Naphthalene Cataract Model in Vitro, *Exp. Eye Res.* 54:73–81 (1992).

Zigler et al., Effects of Lipid Peroxidation Products on the Rat Lens in Organ Culture: A Possible Mechanism of Cataract Initiation in Retinal Degenerative Disease, *Archives of Biochemistry and Biophysics* 225:149–156 (1983).

Zigler et al., Rhesus Monkey Lens as an In Vitro Model for Studying Oxidative Stress, *Investigative Ophthalmology and Visual Science* 30:2195–2199 (1989).

Zigler et al., Prevention of Cataractous Changes in Cultured Rat Lenses by the Hydroxylamine of Tempol (Tempol–H), *Investigative Ophthalmology and Visual Science* 37:211 (1996).

*Primary Examiner*—Zohreh Fay
*Attorney, Agent, or Firm*—Klarquist Sparkman Campbell Leigh & Whinston, LLP

[57] ABSTRACT

A pharmaceutical composition and treatment to inhibit the development of cataracts in the crystalline lens of the eye by administering a hydroxylamine to a subject at risk of developing a cataract. The pharmaceutical composition comprises a hydroxylamine compound in a therapeutically sufficient amount to prevent or retard the development of the cataract. A reducing agent can also be administered in combination with the hydroxylamine. Particular examples of the hydroxylamine are TEMPOL-H, TEMPO-H and OXANO-H, while particular examples of the reducing agent are a sulfhydryl compound, such as N-(2-mercaptopropionyl) glycine (MPG), N-acetyl cysteine, β-mercaptopropionyl glycine, and glutathione. In particular embodiments, the composition comprises TEMPOL-H in an amount that is sufficient to provide a concentration of about 1 $\mu$M to 1 mM in the aqueous humor of the eye, and mercaptopropionyl glycine in an amount sufficient to provide an aqueous humor concentrations of about 0.1 to 5 mM.

19 Claims, 4 Drawing Sheets

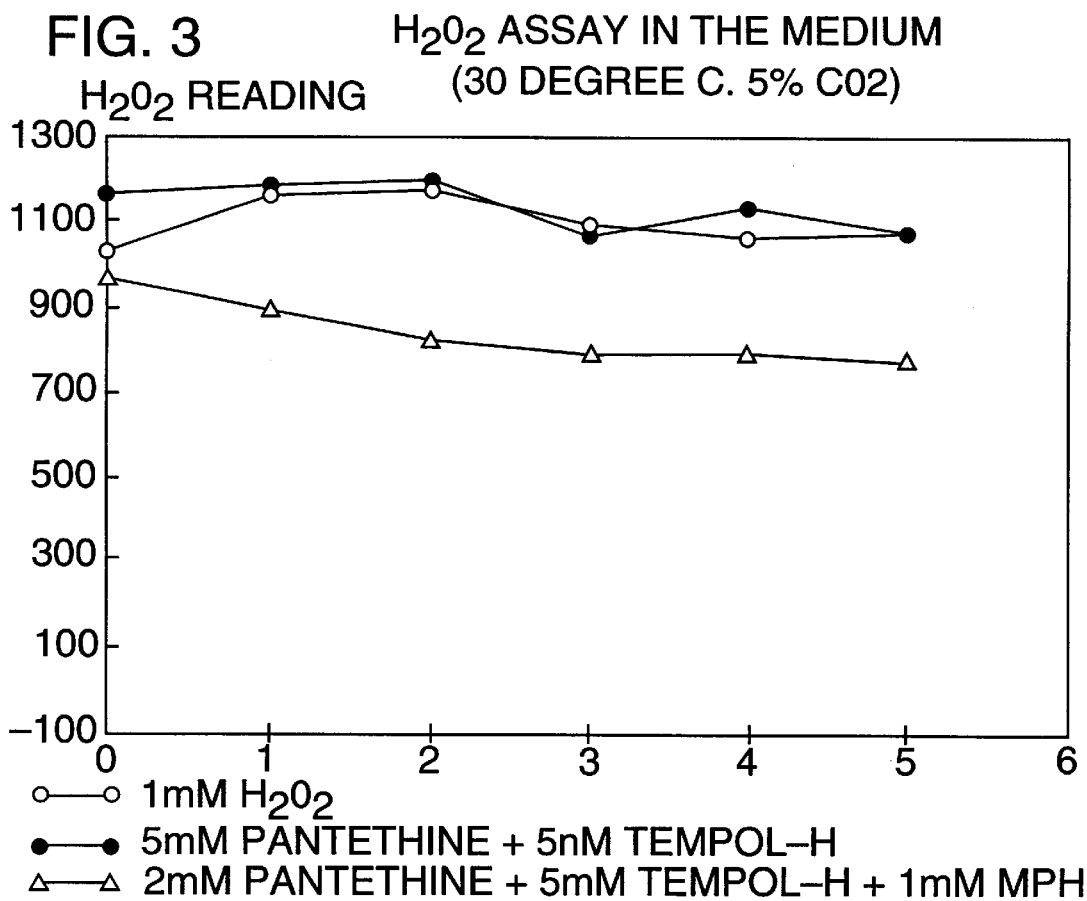
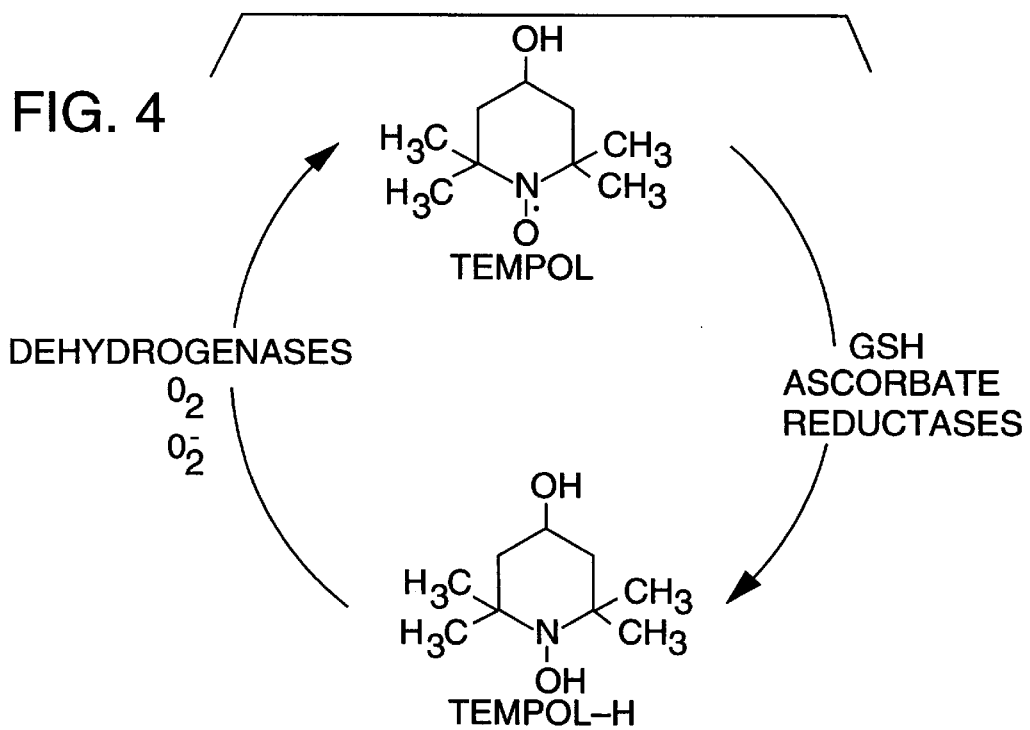

HYDROXYLAMINE COMPOSITIONS FOR THE PREVENTION OR RETARDATION OF CATARACTS

This case claims benefit of Provisional Application 60/010,637 filed Jan. 26, 1997.

BACKGROUND OF THE INVENTION

1. Field of the Invention

The present invention relates to compositions for the prevention and treatment of cataract formation in the crystalline lens of the eye

2. Discussion of the Background

Aging-related cataract is a gradual opacification of the crystalline lens of the eye, which is presently treated by surgical removal and replacement of the cataractous lens. Cataracts are believed to be a disease of multifactorial origin involving many of the same processes that characterize the process of aging in other tissues. Data accumulated over a period of years from the work of many laboratories indicates that once begun, cataract development probably proceeds via one or more common pathways or processes that culminate in damage to lens fibers. Since cataract is already a slowly progressing disease which occurs predominantly in the elderly, a significant retardation of its rate of development could eliminate the need for many surgical cataract extractions. This reduction would provide tremendous benefits both to individual patients and to the public health system.

Based on research from the inventors and others, several processes have been proposed as crucial factors in cataractogenesis. These processes include oxidation, phase separation phenomena and proteolysis. With the hypothesis that one or more of these processes probably represent "common pathways" involved in lens opacification, the inventors initiated an effort to screen compounds which might inhibit these particular processes for their potential as anti-cataract agents. In keeping with the likelihood that the disease is multifactorial, the inventors tested the agents not only individually but in various combinations as well.

One active area of medical research has been an investigation of the role that free radical scavengers and antioxidants may play in the prevention and treatment of diseases caused by oxidative stress. The focus of many such investigations has been upon biochemical pathways that generate reducing power in cells, for example, glutathione synthesis and cycling. Enzymes that reduce activated oxygen species, such as superoxide dismutase, have also been studied to determine whether they diminish cellular oxidative stress. Compounds for inhibiting lipid oxidation in cell membranes by direct radical scavenging have also been considered to be promising therapeutic interventions. The administration of compounds such as vitamin E, carotenoids, selenium compounds and vitamin C (ascorbate), for their antioxidant effects, is known in the popular culture.

There are many reviews in the literature of in vitro and clinical studies of the medical effect of antioxidants and free radical scavengers (references 1–3, below). Thiol compounds have been of particular scientific interest, because glutathione cycling plays a role in maintaining the redox balance in cells. Selenide compounds having glutathione peroxidase activity, for example, are the subject of U.S. Pat. No. 5,321,138. Thiol derivatives of amino acids have also been studied as antioxidants. In particular, mercaptopropionyl glycine (MPG) has been investigated for it effect in reducing cataract formation (4).

In the present invention, the nitroxide family of radicals is of particular interest. Nitroxides are free radicals that are stable, and which are reducible to their corresponding hydroxylamines. Nitroxides were originally of interest to physical chemists due to their paramagnetic properties, allowing their use as "spin-labels" in electron paramagnetic resonance studies. These compounds have more recently been studied because of their radical scavenging properties; nitroxides mimic the enzymatic activity of superoxide dismutase (5–8). Nilsson et al. disclosed, in WO 88/05044, that nitroxides and their corresponding hydroxylamines are useful in prophylaxis and treatment of ischemic cell damage.

Reddan et al. (9) have investigated the use of the nitroxide TEMPOL to protect lens epithelial cells from hydrogen peroxide damage in vitro. Mitchell et al., in U.S. Pat. No. 5,462,946, also disclose use of nitroxides (such as TEMPOL) to protect lens epithelial cells from oxidative damage. However Mitchell and his colleagues have also reported that only the nitroxide TEMPOL protects cells from oxidative damage, and that the corresponding hydroxylamine TEMPOL-H (the reduced nitroxide) affords no such protection (12, 13).

In spite of years of sustained study into the cause and treatment of cataracts, a clinically useful non-surgical treatment that retards the development of age-related cataracts has eluded researchers. Sorbitol-lowering drugs (aldose reductase inhibitors) have been found to have some effect in retarding the development of cataracts in rats with high galactose intake. Aspirin, acetaminophen and ibuprofen have also been shown to delay experimental cataracts. Bendazac has been found to protect lens proteins in vitro, and to delay the onset of cataracts in x-ray irradiated rats. Yet other treatments that have been proposed for the treatment of cataracts include vitamins, aminoguanidine, and various herbal preparations. None of these treatments has yet been demonstrated to be clinically useful.

It is therefore an object of this invention to provide a clinically useful, non-surgical treatment to retard or prevent the development of cataracts in the crystalline lens of the eye.

This and other objects of the invention will be understood more clearly by reference to the following detailed description and drawings.

SUMMARY OF THE INVENTION

The present invention resides in the surprising finding that a hydroxylamine is a better anti-cataractogenic composition than the corresponding nitroxides. This finding is contrary to the teaching of the prior art that hydroxylamines provide much less protection against oxidative damage than corresponding nitroxides. The pharmaceutical compositions of the present invention include a hydroxylamine, or a hydroxylamine and a reducing agent that opposes formation of nitroxides from the hydroxylamines, for prevention and/or treatment of cataracts.

The pharmaceutical composition includes a hydroxylamine compound in a therapeutically sufficient amount to prevent or retard the development of a cataract in a subject to whom the composition is administered. The composition may further include a reducing agent for maintaining the hydroxylamine substantially completely in a reduced form. The reducing agent may be a sulfhydryl compound that is present in a sufficient amount to maintain substantially all the hydroxylamine compound in a reduced state.

In specific embodiments, the reducing agent is selected from the group consisting of mercaptopropionyl glycine, N-acetyl cysteine (NAC), β-mercaptoethylamine and glutathione, and the hydroxylamine compound is selected from the group consisting of TEMPOL-H (the hydroxylamine reduced form of the nitroxide 4-hydroxy-2,2,6,6-tetramethylpiperidin-1-yloxy), TEMPO-H (the hydroxylamine reduced form of the nitroxide 2,2,6,6-tetramethylpiperidin-1-yloxy) and OXANO-H (2-ethyl-2,4,4-trimethyloxazolidine, which is the reduced form of OXANO⁻, 2-ethyl-2,4,4-trimethyloxazolidin-3-yloxy). In the particular preferred embodiment, the sulfhydryl compound is N-(2-mercaptopropionyl) glycine (hereinafter mercaptopropionyl glycine or MPG) and the hydroxylamine compound is TEMPOL-H.

The composition may be a topical preparation or dosage unit form suitable for instillation in the human eye. Such a composition may include TEMPOL-H in an amount that is sufficient to provide TEMPOL-H in a blood concentration of about 25 μM to 3 mM, and mercaptopropionyl glycine in an amount sufficient to provide mercaptopropionyl glycine in a blood concentration of about 0.25 to 50 mM. Alternatively, the composition includes TEMPOL-H in an amount that is sufficient to provide TEMPOL-H in a concentration of about 1 μM to 1 mM in the aqueous humor of the eye, and mercaptopropionyl glycine in an amount sufficient to provide mercaptopropionyl glycine in a concentration of about 0.1 to 5 mM in the aqueous humor of the eye.

The invention also includes a method for inhibiting or preventing the development of a cataract, or inhibiting the progression of an incipient cataract, which comprises administering to a patient a hydroxylamine compound and a reducing agent in a therapeutically sufficient amount to prevent or retard the development of a cataract in a subject to whom the composition is administered. In specific embodiments of the method, the hydroxylamine compound is TEMPOL-H and the reducing agent is mercaptopropionyl glycine. The hydroxylamine and reducing agent may be administered topically, systemically, or intraocularly, and either separately or in combination. Prodrug forms of either the hydroxylamine or reducing agent may be administered, for example to increase corneal penetration. The prodrug could for example be a nitroxide, which is subsequently converted to a hydroxylamine by the reducing agent.

Topical dosage forms include liquid eye drop preparations that may be instilled externally to the eye, or adsorbed into a material such as a soft contact lens or a collagen corneal shield. The hydroxylamine and reducing agent may be introduced into the eye, either separately or in combination, using such forms as topical drops, ointment, periocular (for example subconjunctival) injection, or intraocular instillation (for example by implantation of an intraocular reservoir). The hydroxylamine (and reducing agent if desired) may also be administered orally, in a sufficient amount to raise levels of the drug to desired amounts in the blood or aqueous humor.

BRIEF DESCRIPTION OF THE DRAWINGS

FIG. 3 is a graph showing the lack of interaction of $H_2O_2$ with TEMPOL-H in culture medium.

FIG. 4 is a structural drawing showing the redox cycle between TEMPOL and TEMPOL-H.

DETAILED DESCRIPTION OF THE INVENTION

Figure 1:
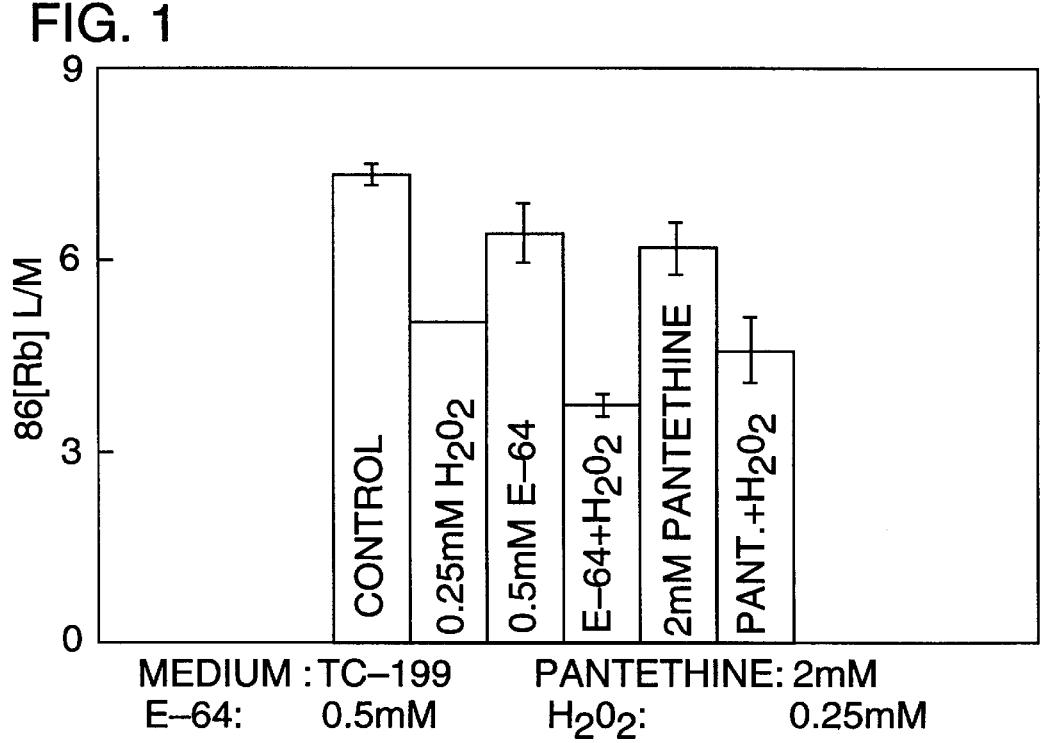
FIG. 1 is a graph showing the effect of $H_2O_2$ treatment on rubidium accumulation by cultured rat lenses.

The pharmaceutical compositions of the present invention include a hydroxylamine compound, or the combination of the hydroxylamine compound and a reducing agent. The hydroxylamine component can be any physiologically acceptable hydroxylamine. Preferable hydroxylamine compounds are monocyclic hydroxylamines wherein the monocycle is an oxazolidine, pyrrolidine or piperidine. Especially preferred hydroxylamines are TEMPO-H, TEMPOL-H and OXANO-H. These compounds possess either a 2,2,6,6-tetramethylpiperidin-1-yloxy structure (the piperidine nitroxide radicals TEMPO⁻ and TEMPOL⁻ which are reduced to the corresponding hydroxylamines TEMPO-H and TEMPOL-H), or the 4,4-dimethyloxazolidin-3-yloxy structure (the oxazolidine nitroxide radical OXANO⁻ that is reduced to the corresponding hydroxylamine OXANO-H).

The reducing agent component of the compositions of the invention functions to maintain the reduced state of the hydroxylamine and/or to provide reducing equivalents directly to the cells of the lens. The reducing agent can be a small organic molecule. Preferable small organic reducing agents are the class of sulfhydryl compounds, such as glutathione. Preferred sulfhydryl compounds are substituted mercapto amino acids, such as mercaptopropionyl glycine. Other sulfhydryl compounds including N-acetyl cysteine, β-mercaptoethylamine and glutathione can also be combined with the hydroxylamine. Precursors of N-acetyl-cysteine can also be used, for example S-isobutyrl-N-acetyl-L-cysteine ethyl ester and other compounds disclosed in U.S. Pat. No. 5,519,054 as prodrugs of N-acetyl-cysteine that are quickly delivered across the cornea Additional compounds of interest can be tested for their cataract-inhibitory activity by testing the composition in the lens organ culture system described in detail in references 10 and 11, and Example 1.

The compositions of the invention are useful for preventing cataract formation, or for treating cataracts, especially by slowing their progression. The compositions can be formulated for prophylactic/therapeutic administration by methods typical in the art, maintaining required sterility and osmolarity. Preferred methods of administration are as eye drops or as an addition to an ophthalmic ointment or lubricant (e.g. DURATEARS, Alcon Ophthalmic). The compositions of the invention can also be adsorbed into dehydrated soft contact lenses (e.g. Lidofilcon B, Bausch & Lomb CW79 or DELTACON (Deltafilcon A)). Alternatively, supports such as a collagen corneal shield (e.g. BIO-COR dissolvable corneal shields, Summit Technology, Watertown, Mass.) could be employed. The compositions can also be administered by infusion into the eyeball, either through a cannula from an osmotic pump (ALZET, Alza Corp., Palo Alto, Calif.) or preferably by implantation of timed-release capsules (OCCUSENT) or biodegradable disks (OCULEX) which contain the compositions. These routes of administration have the advantage of providing a continuous supply of the composition to the eye.

A preferred method of administration will be one which provides for continuous administration to the eye, preferably into the aqueous humor, so that the lens is directly treated. Such methods as delivery by cannula or osmotic pellets are presently most useful, because of their unambiguous delivery to the anterior chamber, in initial testing of the composition. However, as it is expected that long-term, treatment is needed to provide effective therapy, preparations which can be administered topically, i.e. as eye drops or ointments, are most preferred.

The composition is formulated and administered so as to apply a dosage effective for alleviating oxidative stress in the lens of the eye, and/or inhibiting the development of cataracts in the eye. The concentration of the hydroxylamine component will preferably be in the range of 1 $\mu$M to 1 mM in the aqueous humor. Most preferably the range of hydroxylamine concentration will be from 10 to 100 $\mu$M. The concentration of the reducing agent will be from 0.1 to 5 mM in the aqueous humor, preferably in the range of 0.5 to 2 mM. The concentrations of the components of the composition are adjusted appropriately to the route of administration, by typical pharmacokinetic and dilution calculations, to achieve such local concentrations. If the composition is administered systemically, it is estimated that concentrations of 25 $\mu$M to 3 mM of the hydroxylamine component in the blood will be appropriate. A corresponding unit dosage would be 10 to 1200 mg of hydroxylamine per 100 kg body weight. Similarly, systemic administration should seek to achieve a blood concentration of the reducing agent component of 0.25 to 50 mM, corresponding to a unit dose of 100 to 6,000 mg per 100 kg body weight.

Particular embodiments of the invention are illustrated by the Examples set forth below.

EXAMPLE 1
Effect of $H_2O_2$ on Accumulation of Rubidium-86 in Rat Lens

In order to quantitate the effect of drugs that affect cataract development, most assays have used membrane transport (i.e. the ability of the lens to actively transport radiolabelled compounds from the medium) as the test parameter. Normal lenses actively accumulate amino acids, choline or rubidium-86 (Rb-86) from the medium, and the lenses exhibit decrements in such accumulation when the lens epithelium is stressed. Membrane transport assays provide a very sensitive measurement of the health of the lens, and the results indicate changes in lens physiology well before obvious opacification begins. Such assays are accepted as an indication of the in vivo effect of a drug in retarding the development of cataracts.

The techniques described in references 10 and 11 were used in this assay. Rat lenses used in these studies were obtained from Sprague-Dawley male rats. The lenses were incubated in 24-well clusters in modified TC-199 medium (prepared as described in Zigler and Hess, *Exp. Eye Res.* 41:67, 1985) and placed in a 37° C. incubator with a 95% air/5% CO2 humidified atmosphere. The lenses were incubated in about 2.0 ml of culture medium, which was adjusted to about 300 milliosmoles. The assays were usually of 22 hours duration, and tracer levels of $^{86}$Rb or tritiated choline were added at 18 hours so that the tracer was present during the last four hours of the assay.

FIG. 1 gives the results of a representative experiment in which the rat lenses were stressed in organ culture by addition of a bolus of $H_2O_2$ to the medium at the beginning of the assay, equalling a final concentration of 0.25 mM in the initial cultured medium. The normal control lenses were able to accumulate Rb-86 to an internal concentration more than 7-fold greater than the concentration in the medium while those lenses exposed to $H_2O_2$ could accumulate it to only the 5-fold level. Two potential anti-cataract agents were tested in this experiment: E-64 (a protease inhibitor) and panteheine (a putative phase separation inhibitor) were added to the culture medium at the beginning of the assay. Both appeared to have a small negative effect on Rb-86 accumulation when added to the medium of control lenses and neither prevented the decrement in accumulation associated with $H_2O_2$ exposure.

EXAMPLE 2
TEMPOL-H and MPG Inhibit Cataractogenesis by $H_2O_2$

MPG is a sulfhydryl compound and reducing agent which may be acting in part by directly removing $H_2O_2$ from the medium. TEMPOL-H does not react with $H_2O_2$, as shown by the assay of the concentration of $H_2O_2$ in medium containing $H_2O_2$ with and without TEMPOL-H (see the open circle line in FIG. 3). This data indicates that TEMPOL-H is effective intraocularly, i.e. it protects the lens after being taken up into the cells of the lens, particularly the lens epithelium.

TEMPOL-H is the reduced form of the nitroxide TEMPOL, which is a stable free radical detectable by electron paramagnetic resonance (EPR) spectroscopy, as in reference 12. TEMPOL-H can be readily converted to TEMPOL by oxidation with ferricyanide, and then can be quantitated by EPR spectroscopy. This provides a ready means of determining whether TEMPOL-H is present in experimental lenses and whether it is in the oxidized or reduced state. FIG. 4 shows the structure of both compounds and some agents which can effect the redox conversions. That Figure shows that the nitroxide TEMPOL can be reduced to the corresponding hydroxyl TEMPOL-H by reduced glutathione (GSH), ascorbate and reductases. TEMPOL-H can in turn be oxidized to the nitroxide by dehydrogenases and activated oxygen species, such as singlet oxygen.

Figure 2:
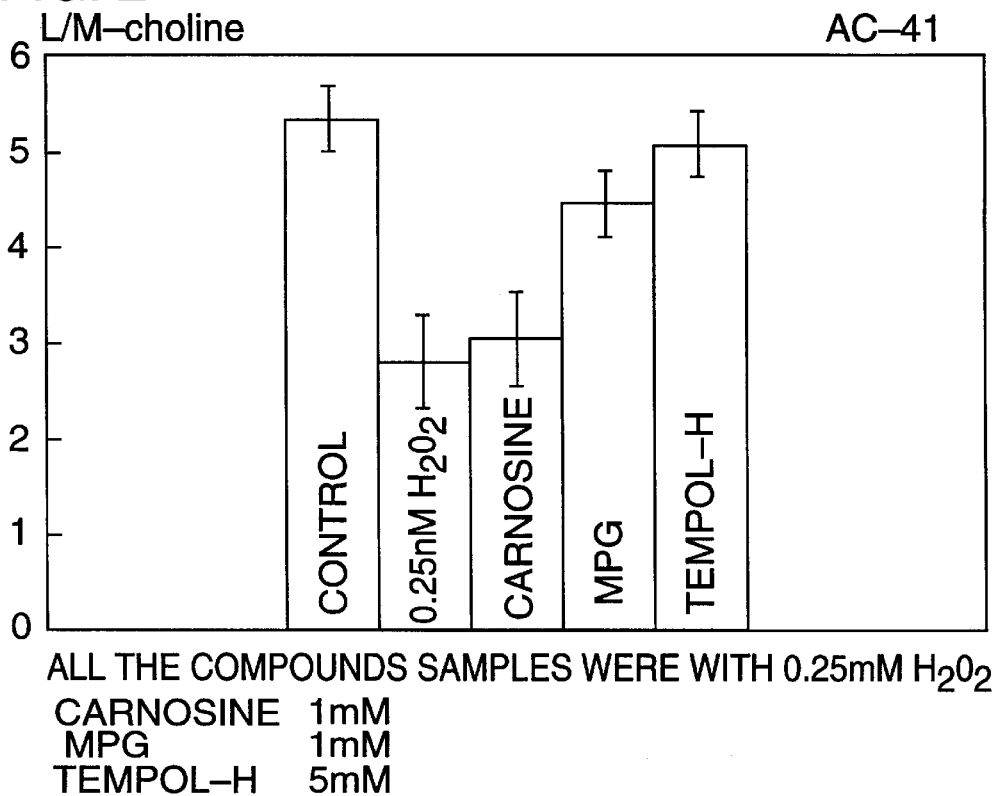
FIG. 2 is a bar graph showing amelioration of $H_2O_2$ inhibition of tritiated choline accumulation by cultured rat lenses as affected by carnosine, MPG and TEMPOL-H.

Rat lenses were cultured as described in reference 11 and Example 1. $H_2O_2$ was added to experimental cultures to a concentration of 0.25 mM. Carnosine at 1 mM, MPG at 1 mM, or TEMPOL-H at 5 mM was added to some of the treated lenses at the beginning of the culture assay. FIG. 2 shows the results of the experiment. Both MPG and TEMPOL-H show significant reduction in the decrement of tritiated choline concentration caused by the $H_2O_2$ treatment.

Following lens incubation, lenses were rinsed, then homogenized in buffer and aliquots of the homogenate analyzed by EPR. Results clearly demonstrated that TEMPOL-H does penetrate the lens from the culture medium and that the highly reducing environment within the lens keeps the compound in the reduced state. Only following treatment of the lens extract with ferricyanide was the nitroxide detected.

EXAMPLE 3
Dose Response of TEMPOL-H and TEMPOL-H with MPG

Figure 5:
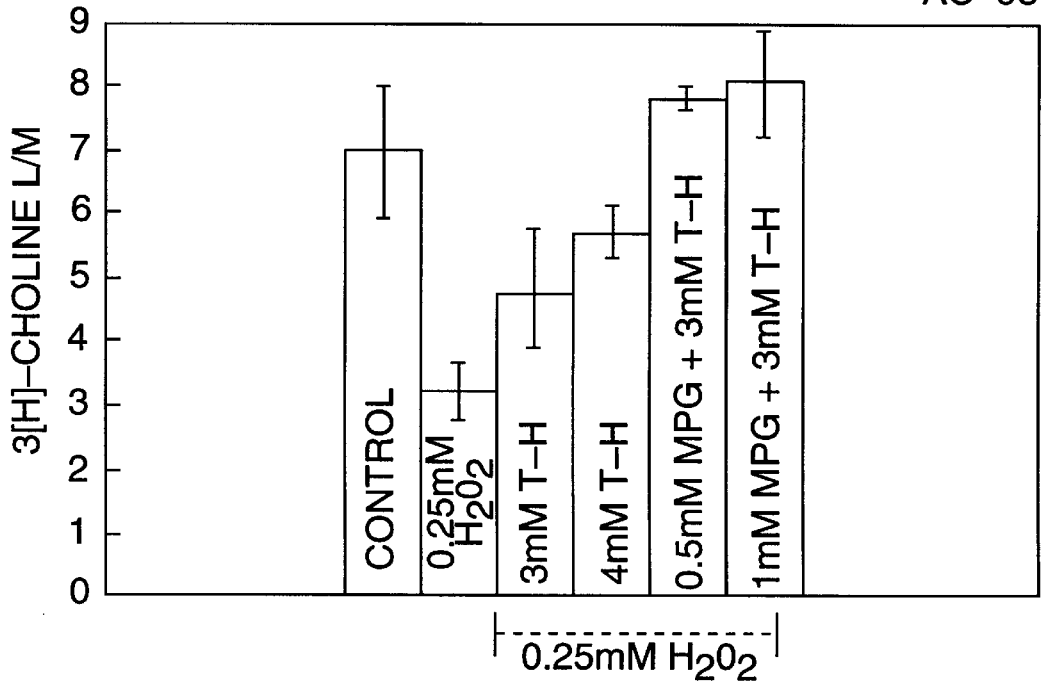
FIG. 5 is a bar graph showing a dose-response effect of TEMPOL-H, and the combination of TEMPOL-H and MPG, in ameliorating $H_2O_2$ inhibition of choline accumulation by cultured rat lenses.
Figure 6:
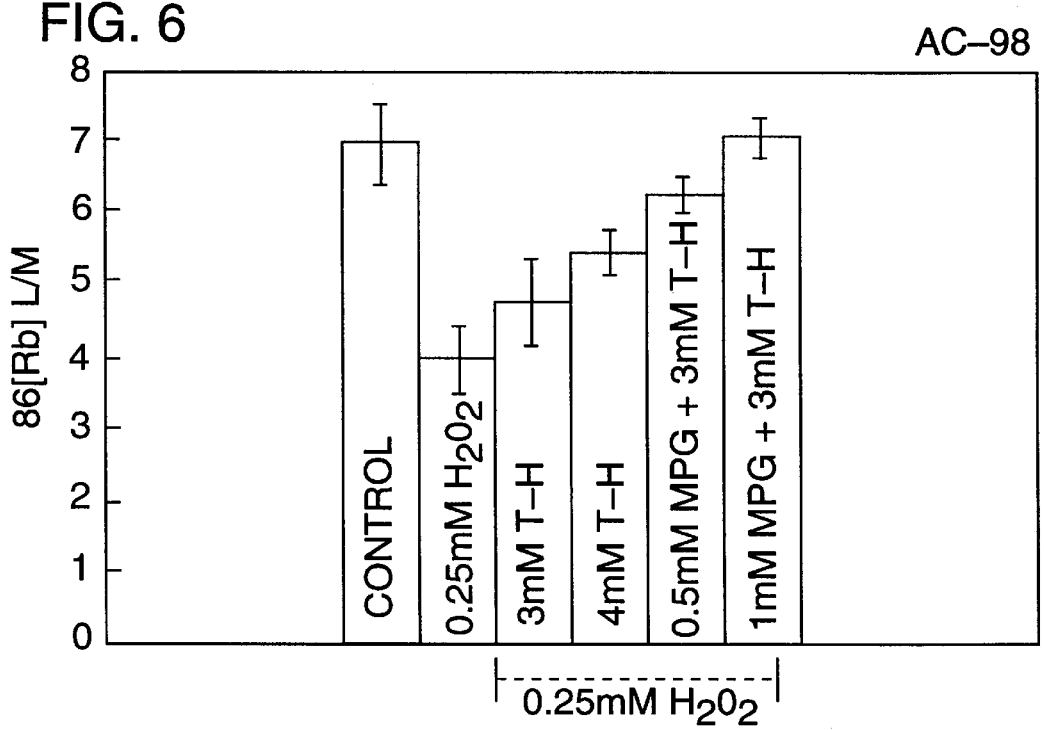
FIG. 6 is a bar graph showing the dose-response effect of TEMPOL-H, and the combination of TEMPOL-H and MPG, in ameliorating $H_2O_2$ inhibition of rubidium accumulation by cultured rat lenses.

FIGS. 5 and 6 provide further data on the effects of TEMPOL-H and MPG on accumulation of $^3$H-choline and Rb-86, respectively, in cultured lenses exposed to $H_2O_2$. The experiment was performed essentially as described for Example 2, except that TEMPOL-H was added at 3 or 4 mM or was added at 3 mM together with MPG at either 0.5 or 1 mM. The data demonstrate a dose response effect for TEMPOL-H and indicate that the combination of TEMPOL-H with MPG has greater efficacy than TEMPOL-H alone. However, even very low concentrations of TEMPOL-H, or TEMPOL-H and MPG, are believed to exert some protective effect against cataract formation.

EXAMPLE 4
TEMPOL-H Prevents Opacification of Cultured Lenses

Figure 7:
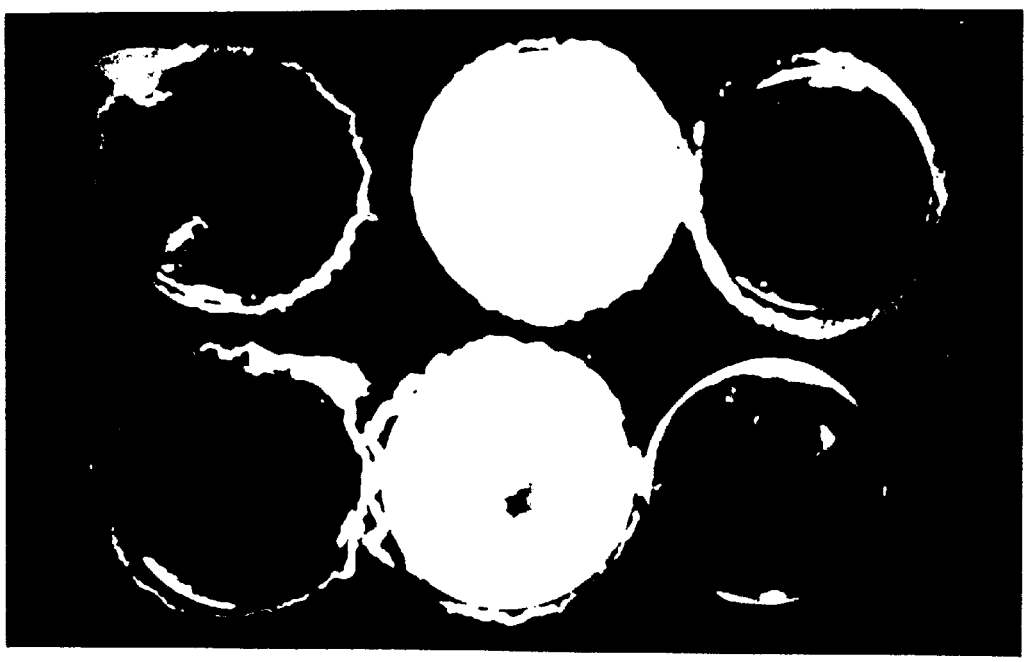
FIG. 7 is a photograph showing opacification of cultured rat lenses by $H_2O_2$ treatment and inhibition of opacification by TEMPOL-H.

Exposure of rat lenses to a bolus of 0.25 mM $H_2O_2$, severely affects membrane transport parameters, but does not cause the lenses to become opaque. However, exposure to 1 mM $H_2O_2$ does produce overt cataract. Lenses were cultured as in the above examples. FIG. 7 shows two control lenses (left pair) after 24 hours incubation in a medium that contains neither $H_2O_2$ nor TEMPOL-H, two lenses incubated for 24 hours in medium to which $H_2O_2$ was added to a concentration of 1.0 mM at time zero (center pair), and two lenses incubated in 1.0 mM $H_2O_2$ plus 4 mM TEMPOL-H (right pair). The TEMPOL-H clearly and consistently was found to inhibit opacification of the cultured lenses, as shown in the right pair of lenses in FIG. 7.

EXAMPLE 5
Method of Treatment

The present invention includes a treatment that inhibits the development of cataracts in a subject such as an animal, for example a rat, rabbit, dog or human. The method includes administering the hydroxylamine, or a combination of the hydroxylamine and a reducing agent, to the subject in a pharmaceutically compatible carrier and in an effective amount to inhibit the development of cataracts in the crystalline lens of the eye. Although the treatment can be used prophylactically in any patient in a demographic group at significant risk for cataracts (for example humans over the age of 55, or subjects of that age who smoke tobacco), subjects can also be selected using more specific criteria. The treatment can be administered, for example, to subjects who have biomicroscopic clinical evidence of an incipient cataract (for example a nuclear sclerotic cataract), or biomicroscopic evidence of a cataract combined with a decrease in visual acuity. Other types of cataracts that would be treated include steroid induced catracts (for example posterior subcapsular cataracts), diabetic cataracts, and cataracts induced by exposure to chemicals or radiation.

The administration of any exogenous TEMPOL-H (or other hydroxylamine) would inhibit the progression of a cataract as compared to a subject to whom the exogenous hydroxylamine was not administered. The anti-cataractogenic effect, however, increases with the dose of the hydroxylamine. In some embodiments of the invention, sufficient hydroxylamine is administered to achieve a concentration in the aqueous humor of at least 1 $\mu$M, more specifically at least 1 mM. In this example, this concentration can be achieved by direct intraocular injection into the anterior chamber of the eye of a 100 mM sterile solution of TEMPOL-H, or delivery of this amount by an implanted pump that delivers a daily intraocular dose of the drug, for example into the anterior chamber of the eye. Paracentesis of the anterior chamber can also be initially or repeatedly performed to determine the concentration of the hydroxylamine in the eye by subjecting the aqueous humor to electron paramagnetic resonance (EPR) studies, as described in reference 11. The information obtained by paracentesis and EPR would then be used to modify the dosage given, or the frequency of administration.

EXAMPLE 6
Topical Delivery

A more clinically convenient treatment would be administration of the hydroxylamine in liquid eye drops, for example a 50 $\mu$L drop of a 100 mM sterile solution of the hydroxylamine TEMPOL-H. Alternatively, the hydroxylamine is administered by direct subconjunctival injection of 1–2 ml of the sterile 100 mM solution, either daily or weekly. Injection of the medication beneath the conjunctiva or Tenon's capsule allows the drug to substantially bypass the conjunctival and corneal epithelial barriers. The eye drops can be formulated in a pharmaceutically inert, biologically acceptable carrier, such as isotonic saline or an ointment. Conventional preservatives, such as benzalkonium chloride, can also be added to the formulation.

The active ingredient it typically dissolved in a buffered, isotonic solution containing antimicrobial preservative agents. In ophthalmic ointments, the active ingredient is admixed with a suitable base, such as white petrolatum and mineral oil, along with antimicrobial preservatives. Ophthalmic disks will typically be constructed to contain a core of active ingredient surrounded by a polymer matrix, such as a hydrophobic ethylene/vinyl acetate copolymer. Specific methods of compounding these dosage forms, as well as appropriate pharmaceutical carriers, are known in the art. REMINGTON PHARMACEUTICAL SCIENCES, 16th Ed., Mack Publishing Co. (1980).

EXAMPLE 7
Systemic Therapy

Experiments were performed with 150–250 gram Sprague Dawley albino rats to demonstrate that systemic delivery of the hydroxylamine and reducing agent could provide intraocular doses of these drugs. A 2 ml volume of 100 mM TEMPOL-H was provided in an ALZET osmotic pump, available from Alza Corporation of Palo Alto, Calif. The pump was programmed to deliver the 2 ml dose continuously (down an osmotic gradient) over a period of either 7 or 14 days. The tip of the pump's delivery cannula was implanted either subcutaneously (on top of the neck of the rat), intraperitoneally, or in the superior fornix of the eye between the upper eyelid and bulbar conjunctiva.

In the rats who received subcutaneous delivery of the hydroxylamine, plasma TEMPOL-H concentrations of 0.25 $\mu$M were observed. Concentrations in the eye were found to be 0.02 $\mu$M. Intraperitoneal delivery provided similar plasma and intraocular concentrations of the drugs.

Alternatively, daily oral dosages of TEMPOL-H could be provided in amounts of 100, 1000 or 6000 mg per 100 kg body weight. The dosages would preferably be given in divided doses, for example four time per day. The oral dosages could be added to food or water. Blood or anterior chamber concentrations of TEMPOL-H can be determined by EPR to adjust the dosage to a desired intraocular concentration.

For the purpose of oral or parenteral administration, the active ingredient may be incorporated into tablets, pills, capsules and the like, which may also contain one or more of the following adjuvants: binders, such as microcrystalline cellulose, gum tragacanth or gelatin; excipients, such as starch or lactose, disintegrating agents such as alginic acid, corn starch and the like; lubricants, such as magnesium stearate; glidants, such as colloidal silicon dioxide; and sweetening agents, such as sucrose. When the dosage unit form is a capsule, it may contain, in addition to the materials of the above type, a liquid carrier such as polyethylene glycol or a fatty oil.

EXAMPLE 8
Systemic Delivery of Reducing Agent

The reducing agent MPG was also delivered to the subjects by subcutaneous, intraperitoneal and ocular routes, as described in Example 7, through an implanted osmotic pump. A 2 ml volume of 100 mM MPG was provided in the pump and delivered over a period of 7 days or 14 days. The MPG was detected in the eye after administration by these routes.

EXAMPLE 9

Concomitant Delivery of Hydroxylamine and Reducing Agent

In those embodiments wherein combined delivery of the hydroxylamine and reducing agent is desired, the hydroxylamine and reducing agent can be administered either separately or in combination. The combined drugs could be delivered, for example, by direct intraocular injection or subconjunctival deposition, or oral ingestion. Alternatively, the hydroxylamine and reducing agent can be delivered separately but at about the same time (for example within about 1 minute of each other).

The delivery of the hydroxylamine could be achieved by any of the routes described in Example 7, and the reducing agent could also be delivered by any of the routes described in Example 8. Hence the TEMPOL-H could be delivered intraperitoneally as described in Example 7, while the MPG could be delivered subcutaneously as in Example 8.

Another approach to delivering the drugs is to provide the hydroxylamine in the form of a nitroxide radical prodrug that is subsequently reduced to the hydroxylamine after moving through the cornea into the anterior chamber. In this example, 100 mM concentration TEMPOL would be administered to the eye in a 50 μL drop instilled in the inferior fornix of the eye. After a period of 5–10 minutes (during which the TEMPOL is allowed to pass through the cornea), 100 mM concentration MPG would be delivered to the eye in a 50 μL drop that is also instilled in the inferior fornix of the eye. The MPG would then pass separately through the cornea, where it would reduce TEMPOL to TEMPOL-H in the aqueous humor of the anterior chamber of the eye.

Some reducing agents, such as N-acetyl-cysteine, do not quickly pass through the cornea. In this situation, the reducing agent may also be administered as a prodrug that is rapidly transported across the corneal barrier into the aqueous humor of the anterior chamber, as in U.S. Pat. No. 5,519,054. Alternatively, the N-acetyl-cysteine could be given orally.

The delivery of drug to the anterior chamber would be repeated daily for the duration of treatment, which could extend throughout the life of the patient, or until surgical extraction and replacement of the lens is required.

The invention being thus described, variation in the materials and methods for practicing the invention will be apparent to one of ordinary skill in the art. Such variations are to be considered within the scope of the invention, which is set forth in the claims below.

REFERENCES

Various articles of the scientific and patent literature are cited throughout the instant document. Each cited article is hereby incorporated by reference in its entirety.

1. B. Halliwell and J. M. C. Gutteridge, *Free Radicals in Biology and Medicine*, 2nd Ed., c. 1989 by Clarendon Press, Oxford.
2. *Oxygen Radicals: Systemic Events and Disease Processes*, D. K. Das and W. B. Essman, eds., c. 1990 by Karger, Basel, Switzerland.
3. C. A. Rice-Evans and A. T. Diplock, *Free Radical Biology & Medicine*, 15:77 (1993).
4. H. Nishigari, *Investigative Ophthalmology & Visual Science*, 25:1051 (1984).
5. U. A. Nilsson et al., *J. Biol. Chem.*, 19:11131 (1989).
6. A. Samuni et al., pp. 85–92 in *Antioxidants in Therapy and Preventive Medicine*, I. Emerit et al., eds. c. 1990 by Plenum Press, New York, N.Y.
7. A. Samuni et al., *J. Clin. Invest.*, 87:1526 (1991).
8. A. Samuni et al., *Biochemistry*, 30:555 (1991).
9. J. R. Reddan et al, *Exp. Eye Res.*, 56:543 (1993).
10. S. J. Tumminia et al., *Exp. Eye Res.*, 58:367 (1994).
11. J. S. Zigler et el., *Investigative Ophthalmology & Visual Science* 30:2195 (1989).
12. Mitchell et al., *Arch. Biochem. Biophys.*, 289:62–70 (1991).
13. Krishna et al., *Cancer Research*, 51:6622–6628 (1991).

We claim:

1. A pharmaceutical composition comprising a hydoxylamine compound in a therapeutically sufficient amount to prevent or retard the development of a cataract in a subject to whom the composition is administered, the composition further comprising a reducing agent for maintaining the hydroxylamine in a reduced form.

2. The composition of claim 1, wherein the reducing agent is a sulfhydryl compound that is present in a sufficient amount to maintain substantially all the hydroxylamine compound in a reduced state.

3. The composition of claim 2, wherein the reducing agent is selected from the group consisting of mercaptopropionyl glycine, N-acetyl cysteine, β-mercaptoethylamine and glutathione.

4. The composition of claim 1, wherein the hydroxylamine compound is selected from the group consisting of TEMPOL-H, TEMPO-H and OXANO-H.

5. The composition of claim 3, wherein the sulfhydryl compound is mercaptopropionyl glycine.

6. The composition of claim 5 wherein the hydroxylamine compound is TEMPOL-H.

7. The composition of claim 1, wherein the composition is a topical preparation suitable for instillation in the human eye.

8. The composition of claim 7, wherein the composition is in a dosage unit form suitable for instillation in or on the human eye.

9. The composition of claim 6, wherein the composition comprises TEMPOL-H in an amount that is sufficient to provide TEMPOL-H in a blood concentration of about 25 μM to 3 mM, and mercaptopropionyl glycine in an amount sufficient to provide mercaptopropionyl glycine in a blood concentration of about 0.25 to 50 mM.

10. The composition of claim 6, wherein the composition comprises TEMPOL-H in an amount that is sufficient to provide TEMPOL-H in a concentration of about 1 μM to 1 mM in aqueous humor of the eye, and mercaptopropionyl glycine in an amount sufficient to provide mercaptopropionyl glycine in a concentration of about 0.1 to 5 mM in aqueous humor of the eye.

11. A pharmaceutical composition comprising a hydroxylamine compound and a reducing agent, for instillation in a human eye to retard or prevent the development of a cataract in a crystalline lens of the eye.

12. The composition of claim 9, where the hydroxylamine compound comprises TEMPOL-H in an amount that is sufficient to provide TEMPOL-H in a concentration of about 1 μM to 1 mM in aqueous humor of the eye, and mercaptopropionyl glycine in an amount sufficient to provide mercaptopropionyl glycine in a concentration of about 0.1 to 5 mM in aqueous humor of the eye.

13. A method for inhibiting or preventing the development of a cataract or inhibiting the progression of an incipient cataract which comprises administering to a patient a hydroxylamine compound and a reducing agent in a therapeutically sufficient amount to prevent or retard the development of a cataract in a subject to whom the composition is administered.

14. The method of claim 13, wherein the step of administering the composition comprises administering TEMPOL-H as the hydroxylamine compound.

15. The method of claim 14, wherein the step of administering the composition comprises administering mercaptopropionyl glycine as the reducing agent.

16. The method of claim 13, wherein the step of administering the composition comprises administering TEMPOL-H in an amount that is sufficient to provide TEMPOL-H in a concentration of about 1 $\mu$M to 1 mM in aqueous humor of the eye, and mercaptopropionyl glycine in an amount sufficient to provide mercaptopropionyl glycine in a concentration of about 0.1 to 5 mM in aqueous humor of the eye.

17. The method of claim 13, wherein the step of administering the composition comprises administering the composition by adsorption into a material selected from the group consisting of a soft contact lens and a collagen corneal shield, and applying said material to the eye.

18. The method of claim 15, wherein the step of administering the composition comprises administering the composition directly to the eye in a topical form selected from the group consisting of eye drops and ointment.

19. A pharmaceutical composition for retarding the development of cataracts in a subject, comprising TEMPOL-H in a therapeutically sufficient amount to prevent or retard the development of a cataract in a subject to whom the composition is administered, a reducing agent comprising mercaptopropionyl glycine in a sufficient amount to maintain the TEMPOL-H substantially completely reduced, and a pharmaceutical carrier suitable for instillation in the human eye.

* * * * *